(12) United States Patent
Patel et al.

(10) Patent No.: US 10,870,714 B2
(45) Date of Patent: Dec. 22, 2020

(54) CAST FILMS, AND ARTICLES MADE THEREFROM

(71) Applicant: Dow Global Technologies LLC, Midland, MI (US)

(72) Inventors: Rajen M. Patel, Lake Jackson, TX (US); Jacquelyn A. Degroot, Sugar Land, TX (US); Fabricio Arteaga Larios, Sugar Land, TX (US); Selim Bensason, Rueschlikon (CH); Teresa P. Karjala, Lake Jackson, TX (US); Mehmet Demirors, Pearland, TX (US); Chuan Yar Lai, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 204 days.

(21) Appl. No.: 16/066,868

(22) PCT Filed: Jan. 25, 2017

(86) PCT No.: PCT/US2017/014901
§ 371 (c)(1),
(2) Date: Jun. 28, 2018

(87) PCT Pub. No.: WO2017/139096
PCT Pub. Date: Aug. 17, 2017

(65) Prior Publication Data
US 2019/0002602 A1 Jan. 3, 2019

Related U.S. Application Data

(60) Provisional application No. 62/294,546, filed on Feb. 12, 2016.

(51) Int. Cl.
| | | |
|---|---|---|
| *C08F 210/16* | (2006.01) | |
| *C08F 10/02* | (2006.01) | |
| *C08L 23/16* | (2006.01) | |
| *C08J 5/18* | (2006.01) | |
| *C08L 23/08* | (2006.01) | |
| *C08L 23/04* | (2006.01) | |
| *A61L 15/24* | (2006.01) | |
| *A61L 31/04* | (2006.01) | |
| *B32B 5/02* | (2006.01) | |
| *B32B 27/12* | (2006.01) | |
| *B32B 27/32* | (2006.01) | |
| *C08K 3/22* | (2006.01) | |

(52) U.S. Cl.
CPC ............ *C08F 10/02* (2013.01); *A61L 15/24* (2013.01); *A61L 31/048* (2013.01); *B32B 5/022* (2013.01); *B32B 27/12* (2013.01); *B32B 27/32* (2013.01); *C08J 5/18* (2013.01); *C08L 23/04* (2013.01); *C08L 23/08* (2013.01); *C08L 23/16* (2013.01); *C08J 2323/06* (2013.01); *C08J 2323/08* (2013.01); *C08K 2003/2241* (2013.01); *C08L 2205/02* (2013.01); *C08L 2207/066* (2013.01)

(58) Field of Classification Search
CPC .... C08F 210/16; C08F 10/02; C08F 2500/07; C08F 2500/12; C08F 2500/26; C08L 23/06; C08L 23/08; C08L 23/16; C08L 23/0815; C08L 2203/14; C08L 2203/16
See application file for complete search history.

(56) References Cited

U.S. PATENT DOCUMENTS

| | | | |
|---|---|---|---|
| 4,599,392 A | | 7/1986 | McKinney et al. |
| 5,395,471 A † | | 3/1995 | Obijeski |
| 7,498,282 B2 | | 3/2009 | Patel et al. |
| 8,372,931 B2 | | 2/2013 | Hermel-Davidock et al. |
| 8,889,794 B2 * | | 11/2014 | Wang .................. C08J 5/18 525/240 |
| 9,000,096 B2 * | | 4/2015 | Brodil .................. C08L 23/06 525/240 |
| 9,255,160 B2 * | | 2/2016 | Desjardins ............. C08J 5/18 |
| 9,828,476 B2 * | | 11/2017 | Bensason ............. B32B 27/205 |
| 2013/0072632 A1 | | 3/2013 | Wang et al. |
| 2014/0080970 A1 † | | 3/2014 | Desjardins |
| 2014/0178614 A1 | | 6/2014 | Demirors et al. |

(Continued)

FOREIGN PATENT DOCUMENTS

| | | |
|---|---|---|
| CA | 2798854 A1 | 6/2014 |
| WO | 1993003093 | 2/1993 |

(Continued)

OTHER PUBLICATIONS

Williams, J. Polym. Sci., Polym. Let., 1968, vol. 6, p. 621.
Monrabal, Macromol. Symp., 2007, vol. 257, p. 71-79.
PCT/US2017/014901, International Search Report and Written Opinion dated Apr. 24, 2017.
PCT/US2017/014901, International Preliminary Report on Patentability dated Aug. 23, 2018.

*Primary Examiner* — Rip A Lee

(57) ABSTRACT

Disclosed herein is a cast film comprising a polyethylene composition comprising the reaction product of ethylene and optionally one or more alpha-olefin comonomers, wherein said polyethylene composition is characterized by the following properties: a melt index, I2, measured according to ASTM D1238 (2.16 kg, 190° C.), of from 1 to 20 g/10 min; a density (measured according to ASTM D792) of from 0.935 to 0.970 g/cm3; a melt flow ratio, $I_{10}/I_2$, wherein $I_{10}$ is measured according to ASTM D1238 (10 kg, 190° C.) of from 5.5 to 7.0; a molecular weight distribution (Mw/Mn) of from 2.2 to 3.5; and a vinyl unsaturation of greater than 0.12 vinyls per one thousand carbon atoms present in the backbone of the composition.

11 Claims, No Drawings

(56) References Cited

U.S. PATENT DOCUMENTS

2015/0344681 A1* 12/2015 Kapur ................. C08L 23/0815
                                                                525/240
2017/0008985 A1    1/2017 Demirors et al.
2017/0129230 A1*  5/2017 Wang ..................... B32B 27/32
2018/0010304 A1    1/2018 Bonavoglia et al.

FOREIGN PATENT DOCUMENTS

| WO | 2005023912 A2 | 3/2005 |
| WO | 2012166093 A1 | 12/2012 |
| WO | 2012166469 A1 | 12/2012 |
| WO | 2015034804 A1 | 3/2015 |

\* cited by examiner
† cited by third party

CAST FILMS, AND ARTICLES MADE THEREFROM

TECHNICAL FIELD

Embodiments of the present disclosure generally relate to cast films and applications of the cast films to make hygiene and medical articles. In particular, this disclosure relates to non-breathable cast films.

BACKGROUND

Polyethylene films are widely used in hygiene absorbent products, such as, for example, diaper backsheets. Diaper backsheets may be classified as breathable or non-breathable. Breathable backsheets typically use films that are $CaCO_3$ filled and/or microcavitated. Non-breathable backsheet films may typically be made from blends of high density polyethylene (HDPE) or linear low density polyethylene (LLDPE) and low density polyethylene (LDPE).

There is a desire to downgauge non-breathable backsheet films while ensuring good processability/line speed and properties. Currently Ziegler-Natta (Z-N) HDPE and/or LLDPE resins used to make non-breathable backsheet have reached its downgauging limit. Attempts to further downgauge these resins can significantly compromise film stiffness, toughness, and line speed during manufacturing.

Accordingly, alternative non-breathable backsheet films of high modulus, tensile strength, and toughness (impact/puncture/tear resistance) are desired to further allow for downgauging.

SUMMARY

Disclosed in embodiments herein are cast films. The cast films comprise a polyethylene composition comprising the reaction product of ethylene and optionally one or more alpha-olefin comonomers, wherein said polyethylene composition is characterized by the following properties: a melt index, $I_2$, measured according to ASTM D1238 (2.16 kg, 190° C.), of from 1 to 20 g/10 min; a density (measured according to ASTM D792) of from 0.935 to 0.970 g/cm3; a melt flow ratio, $I_{10}/I_2$, wherein $I_{10}$ is measured according to ASTM D1238 (10 kg, 190° C.) of from 5.5 to 7.0; a molecular weight distribution (Mw/Mn) of from 2.2 to 3.5; and a vinyl unsaturation of greater than 0.12 vinyls per one thousand carbon atoms present in the backbone of the composition.

Also disclosed herein are laminates or articles comprising a cast film. The cast film comprises a polyethylene composition comprising the reaction product of ethylene and optionally one or more alpha-olefin comonomers, wherein said polyethylene composition is characterized by the following properties: a melt index, $I_2$, measured according to ASTM D1238 (2.16 kg, 190° C.), of from 1 to 20 g/10 min; a density (measured according to ASTM D792) of from 0.935 to 0.970 g/cm3; a melt flow ratio, $I_{10}/I_2$, wherein $I_{10}$ is measured according to ASTM D1238 (10 kg, 190° C.) of from 5.5 to 7.0; a molecular weight distribution (Mw/Mn) of from 2.2 to 3.5; and a vinyl unsaturation of greater than 0.12 vinyls per one thousand carbon atoms present in the backbone of the composition.

Additional features and advantages of the embodiments will be set forth in the detailed description which follows, and in part will be readily apparent to those skilled in the art from that description or recognized by practicing the embodiments described herein, including the detailed description which follows, the claims. It is to be understood that both the foregoing and the following description describe various embodiments and are intended to provide an overview or framework for understanding the nature and character of the claimed subject matter. The description serves to explain the principles and operations of the claimed subject matter.

DETAILED DESCRIPTION

Reference will now be made in detail to embodiments of non-breathable films (hereinafter called "films") and laminates, examples of which are further described below. The films may be used to produce film backsheet with the right balance of stiffness and toughness. It is noted, however, that this is merely an illustrative implementation of the embodiments disclosed herein. The embodiments are applicable to other technologies that are susceptible to similar problems as those discussed above. For example, the films may be used to produce clothlike backsheets, medical gowns, medical drapes, table covers are all clearly within the purview of the present embodiments. The film may be a monolayer film or a multilayer film. As used herein, "multilayer film" refers to a film having two or more layers that are at least partially contiguous and preferably, but optionally, coextensive. The film is a cast film. In some embodiments, the cast film may be a cast embossed film.

In embodiments herein, the film comprises a polyethylene composition. The film comprises from 50 to 100 percent, 55 to 100 percent, 60 to 100 percent, 65 to 100 percent, 70 to 100 percent, 75 to 100 percent, 80 to 100 percent, 85 to 100 percent, 90 to 100 percent, or 95 to 100 percent, by total weight of polymers present in the film, of the polyethylene composition.

The polyethylene composition comprises the reaction product of ethylene and optionally one or more alpha-olefin comonomers. The polyethylene composition comprises greater than 50 wt. % of the units derived from ethylene and less than 30 wt. % of the units derived from one or more alpha-olefin comonomers. In some embodiments, the polyethylene composition comprises (a) greater than or equal to 55%, for example, greater than or equal to 60%, greater than or equal to 65%, greater than or equal to 70%, greater than or equal to 75%, greater than or equal to 80%, greater than or equal to 85%, greater than or equal to 90%, greater than or equal to 92%, greater than or equal to 95%, greater than or equal to 97%, greater than or equal to 98%, greater than or equal to 99%, greater than or equal to 99.5%, from greater than 50% to 99%, from greater than 50% to 97%, from greater than 50% to 94%, from greater than 50% to 90%, from 70% to 99.5%, from 70% to 99%, from 70% to 97% from 70% to 94%, from 80% to 99.5%, from 80% to 99%, from 80% to 97%, from 80% to 94%, from 80% to 90%, from 85% to 99.5%, from 85% to 99%, from 85% to 97%, from 88% to 99.9%, 88% to 99.7%, from 88% to 99.5%, from 88% to 99%, from 88% to 98%, from 88% to 97%, from 88% to 95%, from 88% to 94%, from 90% to 99.9%, from 90% to 99.5% from 90% to 99%, from 90% to 97%, from 90% to 95%, from 93% to 99.9%, from 93% to 99.5% from 93% to 99%, or from 93% to 97%, by weight, of the units derived from ethylene; and (b) optionally, less than 30 percent, for example, less than 25 percent, or less than 20 percent, less than 18%, less than 15%, less than 12%, less than 10%, less than 8%, less than 5%, less than 4%, less than 3%, less than 2%, less than 1%, from 0.1 to 20%, from 0.1 to 15%, 0.1 to 12%, 0.1 to 10%, 0.1 to 8%, 0.1 to 5%, 0.1 to 3%, 0.1 to 2%, 0.5 to 12%, 0.5 to 10%, 0.5 to 8%, 0.5 to 5%, 0.5 to 3%, 0.5 to 2.5%, 1 to 10%, 1 to 8%, 1 to 5%, 1 to 3%, 2 to 10%, 2 to 8%, 2 to 5%, 3.5 to 12%, 3.5 to 10%, 3.5 to 8%, 3.5% to 7%, or 4 to 12%, 4 to 10%, 4 to 8%, or 4 to 7%, by weight, of units derived from one or more a-olefin comonomers. The comonomer content may be measured using any suitable technique, such as techniques based on nuclear magnetic resonance ("NMR") spectroscopy, and, for example, by 13C NMR analysis as described in U.S. Pat. No. 7,498,282, which is incorporated herein by reference.

Suitable comonomers may include alpha-olefin comonomers, typically having no more than 20 carbon atoms. The one or more alpha-olefins may be selected from the group consisting of C3-C20 acetylenically unsaturated monomers and C4-C18 diolefins. Those skilled in the art will understand that the selected monomers are desirably those that do not destroy conventional Ziegler-Natta catalysts. For example, the alpha-olefin comonomers may have 3 to 10 carbon atoms, or 3 to 8 carbon atoms. Exemplary alpha-olefin comonomers include, but are not limited to, propylene, 1-butene, 1-pentene, 1-hexene, 1-heptene, 1-octene, 1-nonene, 1-decene, and 4-methyl-1-pentene. The one or more alpha-olefin comonomers may, for example, be selected from the group consisting of propylene, 1-butene, 1-hexene, and 1-octene; or in the alternative, from the group consisting of 1-butene, 1-hexene and 1-octene. In some embodiments, the polyethylene composition comprises greater than 0 wt. % and less than 30 wt. % of units derived from one or more of octene, hexene, or butene comonomers.

In some embodiments, the polyethylene composition is formed in the presence of a catalyst composition comprising a multi-metallic procatalyst via solution polymerization in at least one reactor. In other embodiments, the polyethylene composition is formed in the presence of a catalyst composition comprising a multi-metallic procatalyst comprising of three or more transition metals via solution polymerization in at least one reactor. In some embodiments, the solution polymerization occurs in a single reactor. The multi-metallic procatalyst used in producing the reaction product is at least trimetallic, but may also include more than three transition metals, and thus may in one embodiment be defined more comprehensively as multi-metallic. These three, or more, transition metals are selected prior to production of the catalyst. In a particular embodiment, the multi-metal catalyst comprises titanium as one element.

The catalyst compositions may be prepared beginning first with preparation of a conditioned magnesium halide-based support. Preparation of a conditioned magnesium halide-based support begins with selecting an organomagnesium compound or a complex including an organomagnesium compound. Such compound or complex is desirably soluble in an inert hydrocarbon diluent. The concentrations of components are preferably such that when the active halide, such as a metallic or non-metallic halide, and the magnesium complex are combined, the resultant slurry is from about 0.005 to about 0.25 molar (moles/liter) with respect to magnesium. Examples of suitable inert organic diluents include liquefied ethane, propane, isobutane, n-butane, n-hexane, the various isomeric hexanes, isooctane, paraffinic mixtures of alkanes having from 5 to 10 carbon atoms, cyclohexane, methylcyclopentane, dimethylcyclohexane, dodecane, industrial solvents composed of saturated or aromatic hydrocarbons such as kerosene, naphthas, and combinations thereof, especially when freed of any olefin compounds and other impurities, and especially those having boiling points in the range from about −50° C. to about 200° C. Also included as suitable inert diluents are ethylbenzene, cumene, decalin and combinations thereof.

Suitable organomagnesium compounds and complexes may include, for example, magnesium C2-C8 alkyls and aryls, magnesium alkoxides and aryloxides, carboxylated magnesium alkoxides, and carboxylated magnesium aryloxides. Preferred sources of magnesium moieties may include the magnesium C2-C8 alkyls and C1-C4 alkoxides. Such organomagnesium compound or complex may be reacted with a metallic or non-metallic halide source, such as a chloride, bromide, iodide, or fluoride, in order to make a magnesium halide compound under suitable conditions. Such conditions may include a temperature ranging from −25° C. to 100° C., alternatively, 0° C. to 50° C.; a time ranging from 1 to 12 hours, alternatively, from 4 to 6 hours; or both. The result is a magnesium halide based support.

The magnesium halide support is then reacted with a selected conditioning compound containing an element selected from the group consisting of boron, aluminum, gallium, indium and tellurium, under conditions suitable to form a conditioned magnesium halide support. This compound and the magnesium halide support are then brought into contact under conditions sufficient to result in a conditioned magnesium halide support. Such conditions may include a temperature ranging from 0° C. to 50° C., or alternatively, from 25° C. to 35° C.; a time ranging from 4 to 24 hours, or alternatively, from 6 to 12 hours; or both. The conditioning compound has a molar ratio constitution that is specific and which is believed to be an important feature in ensuring the desirable catalyst performance. Specifically, the procatalyst desirably exhibits a molar ratio of the magnesium to the conditioning compound that ranges from 3:1 to 6:1. Without wishing to be bound by any theory of mechanism, it is suggested that this aging serves to facilitate or enhance adsorption of additional metals onto the support.

Once the conditioned support is prepared and suitably aged, it is brought into contact with a titanium compound which may be added individually or as a mixture with the "second metal". In certain preferred embodiments titanium halides or alkoxides, or combinations thereof, may be selected. Conditions may include a temperature within the range from 0° C. to 50° C., alternatively from 25° C. to 35° C.; a time from 3 hours to 24 hours, alternatively from 6 hours to 12 hours; or both. The result of this step is adsorption of at least a portion of the titanium compound onto the conditioned magnesium halide support.

Finally, one or two additional metals, referred to herein as "the second metal" and "the third metal" for convenience, will also be adsorbed onto the magnesium-based support, The "second metal" and the "third metal" are independently selected from zirconium (Zr), hafnium (Hf), vanadium (V), niobium (Nb), tantalum (Ta), chromium (Cr), molybdenum (Mo), and tungsten (W). These metals may be incorporated in any of a variety of ways known to those skilled in the art, but generally contact between the conditioned magnesium based halide support including titanium and the selected second and third metals, in, e.g., liquid phase such as an appropriate hydrocarbon solvent, will be suitable to ensure deposition of the additional metals to form what may now be referred to as the "procatalyst," which is a multi-metallic procatalyst.

The multi-metallic procatalyst has a molar ratio constitution that is specific and which is believed to be an important feature in ensuring the desirable polymer properties that may be attributed to the catalyst made from the procatalyst. Specifically, the procatalyst desirably exhibits a molar ratio of the magnesium to a combination of the titanium and the second and third metals that ranges from 30:1 to 5:1; under conditions sufficient to form a multi-metallic procatalyst.

Thus, the overall molar ratio of magnesium to titanium ranges from 8:1 to 80:1. In some embodiments, the Al:Ti ratio is from 6 to 15, 7 to 14, 7 to 13, 8 to 13, 9 to 13, or 9 to 12.

Once the procatalyst has been formed, it may be used to form a final catalyst by combining it with a cocatalyst consisting of at least one organometallic compound such as an alkyl or haloalkyl of aluminum, an alkylaluminum halide, a Grignard reagent, an alkali metal aluminum hydride, an alkali metal borohydride, an alkali metal hydride, an alkaline earth metal hydride, or the like. The formation of the final catalyst from the reaction of the procatalyst and the organometallic cocatalyst may be carried out in situ, or just prior to entering the polymerization reactor. Thus, the combination of the cocatalyst and the procatalyst may occur under a wide variety of conditions. Such conditions may include, for example, contacting them under an inert atmosphere such as nitrogen, argon or other inert gas at temperatures in the range from 0° C. to 250° C., preferably from 15° C. to 200° C. In the preparation of the catalytic reaction product, it is not necessary to separate hydrocarbon soluble components from hydrocarbon insoluble components. Time for contact between the procatalyst and cocatalyst may desirably range, for example, from 0 to 240 seconds, preferably from 5 to 120 seconds. Various combinations of these conditions may be employed.

In embodiments described herein, the polyethylene composition may have a metal catalyst residual of greater than or equal to 1 parts by combined weight of at least three metal residues per one million parts of polyethylene polymer, wherein the at least three metal residues are selected from the group consisting of titanium, zirconium, hafnium, vanadium, niobium, tantalum, chromium, molybdenum, tungsten, and combinations thereof, and wherein each of the at least three metal residues is present at greater than or equal to 0.2 ppm, for example, in the range of from 0.2 to 5 ppm. All individual values and subranges from greater than or equal to 0.2 ppm are included herein and disclosed herein; for example, the polyethylene composition may further comprise greater than or equal to 2 parts by combined weight of at least three metal residues remaining from the multi-metallic polymerization catalyst per one million parts of the polyethylene composition.

In some embodiments, the polyethylene composition comprises at least 0.75 ppm of V (Vanadium). All individual values and subranges from at least 0.75 ppm of V are included and disclosed herein; for example the lower limit of the V in the polyethylene composition may be 0.75, 1, 1.1, 1.2, 1.3 or 1.4 ppm to an upper limit of the V in the polyethylene composition may be 5, 4, 3, 2, 1.9, 1.8, 1.7, 1.6, 1.5, or 1 ppm. The vanadium catalyst metal residual concentration for the polyethylene composition can be measured using the Neutron Activation Method for Metals described below.

In some embodiments, the polyethylene composition comprises at least 0.3 ppm of Zr (Zirconium). All individual values and subranges of at least 0.3 ppm of Zr are included and disclosed herein; for example the lower limit of the Zr in the polyethylene composition may be 0.3, 0.4, 0.5, 0.6 or 0.7 ppm. In yet another embodiment, the upper limit of the Zr in the polyethylene composition may be 5, 4, 3, 2, 1, 0.9, 0.8 or 0.7 ppm. The zirconium catalyst metal residual concentration for the polyethylene composition can be measured using the Neutron Activation Method for Metals described below.

In embodiments described herein, the polyethylene composition has a density of 0.935 g/cm$^3$ to 0.970 g/cm$^3$. All individual values and subranges of at least 0.935 g/cm$^3$ to 0.970 g/cm$^3$ are included and disclosed herein. For example, in some embodiments, the polyethylene composition may have a density ranging from a lower limit of 0.935, 0.937, 0.938, 0.940, 0.942, 0.945, 0.946, or 0.947 g/cm$^3$ to an upper limit of 0.968, 0.967, 0.965, 0.963, or 0.962 g/cm$^3$. In other embodiments, the polyethylene composition may have a density of 0.935 to 0.967 g/cm$^3$, 0.940 to 0.970 g/cm$^3$, 0.942 to 0.967 g/cm$^3$, 0.942 to 0.965 g/cm$^3$, 0.945 to 0.965 g/cm$^3$, or 0.945 to 0.963 g/cm$^3$. In further embodiments, the polyethylene composition may have a density of from 0.945 to 0.970 g/cm$^3$, 0.947 to 0.970 g/cm$^3$, 0.950 to 0.970 g/cm$^3$, 0.9520 to 0.970 g/cm$^3$, 0.952 to 0.968 g/cm$^3$, 0.9550 to 0.970 g/cm$^3$, or 0.955 to 0.965 g/cm$^3$. Density may be measured in accordance with ASTM D792.

In embodiments described herein, the polyethylene composition has a melt index, $I_2$, of 1 g/10 min to 20 g/10 min. All individual values and subranges of at least 1 g/10 min to 20 g/10 min are included and disclosed herein. For example, in some embodiments, the polyethylene composition may have melt index, $I_2$, ranging from a lower limit of 1.0, 1.5, 2.0, 2.5, 3.0, 3.4, 3.5, 4.0, or 4.5 to an upper limit of 20, 19, 18, 17, 16, 15, 14, 13, 12, 11, 10, 9, 8, or 7 g/10 min. In other embodiments, the polyethylene composition may have a melt index, $I_2$, of 1.0 g/10 min to 18 g/10 min, 1.0 g/10 min to 16 g/10 min, or 1.0 g/10 min to 15 g/10 min. In further embodiments, the polyethylene composition may have a melt index, $I_2$, 2.0 g/10 min to 20 g/10 min, 2.0 g/10 min to 18 g/10 min, or 2.0 g/10 min to 15 g/10 min. In further embodiments, the polyethylene composition may have a melt index, $I_2$, 2.5 g/10 min to 15 g/10 min, 2.5 g/10 min to 10 g/10 min, or 2.7 g/10 min to 10 g/10 min. In even further embodiments, the polyethylene composition may have a melt index, $I_2$, 4.0 g/10 min to 20 g/10 min, 4.0 g/10 min to 15 g/10 min, 4.0 g/10 min to 10 g/10 min, 4.0 g/10 min to 8 g/10 min, 5.0 g/10 min to 8 g/10 min, or 5.0 g/10 min to 7 g/10 min. Melt index, $I_2$, may be measured in accordance with ASTM D1238 (190° C. and 2.16 kg).

In embodiments described herein, the polyethylene composition has a melt flow ratio, $I_{10}/I_2$, of from 5.5 to 7.0. All individual values and subranges of from 5.5 to 7.0 are included and disclosed herein. For example, in some embodiments, the polyethylene composition may have a melt flow ratio, $I_{10}/I_2$, ranging from a lower limit of 5.5, 5.6, 5.7, 5.8, 5.9, 6.0, 6.1, or 6.2 to an upper limit of 7.0, 6.8, 6.7, 6.6, 6.5, 6.4, or 6.35. In other embodiments, the polyethylene composition may have a melt flow ratio, $I_{10}/I_2$, of from 5.6 to 7.0, 5.7 to 6.8, 5.8 to 6.8, 5.9 to 6.8, or 6.0 to 6.7. In further embodiments, the polyethylene composition may have a melt flow ratio, I10/I2, of from 5.5 to 6.7, 5.6 to 6.7, 5.8 to 6.7, or 6.0 to 6.6. Melt index, $I_{10}$, may be measured in accordance with ASTM D1238 (190° C. and 10.0 kg).

In embodiments described herein, the polyethylene composition has a molecular weight distribution (Mw/Mn) of from 2.2 to 3.5. All individual values and subranges of from 2.2 to 3.5 are included and disclosed herein. For example, the polyethylene composition may have an Mw/Mn ratio from a lower limit of 2.2, 2.3, 2.4, 2.5, 2.6, 2.7, or 2.8 to an upper limit of 3.5, 3.4, 3.3, 3.2, 3.1, 3.0, or 2.9. In some embodiments, the polyethylene composition may have an Mw/Mn ratio of from 2.2 to 3.5, 2.3 to 3.5, 2.4 to 3.5, 2.4 to 3.2, 2.5 to 3.2, or 2.6 to 3.1. In other embodiments, the polyethylene composition may have an Mw/Mn ratio of from 2.3 to 3.0, 2.4 to 3.0, 2.5 to 3.0, 2.6 to 3.0, or 2.7 to 3.0. Molecular weight distribution can be described as the ratio of weight average molecular weight ($M_w$) to number average molecular weight ($M_n$) (i.e., $M_w/M_n$), and can be measured by gel permeation chromatography techniques.

In embodiments described herein, the polyethylene composition has a vinyl unsaturation of greater than 0.12 vinyls per one thousand carbon atoms ("1000C") present in the backbone of the composition. All individual values and subranges from greater than 0.12 vinyls per 1000 carbon atoms are included and disclosed herein. In some embodiments, the polyethylene composition may have greater than or equal to 0.13, 0.14, 0.15, or 0.16 vinyls per 1000 carbon atoms. In other embodiments, the polyethylene composition may have vinyls per 1000 carbon atoms ranging from a lower limit of greater than 0.12, 0.13, 0.14, 0.15, 0.16, or 0.17 to an upper limit of 0.50, 0.45, 0.40, 0.35, 0.30, 0.26, 0.25, 0.24, 0.23, 0.22, 0.21, or 0.20. In further embodiments, the polyethylene composition may have greater than 0.12 to 0.50, 0.13 to 0.45, 0.14 to 0.40, 0.14 to 0.35, 0.14 to 0.30, 0.14 to 0.25, or 0.15 to 0.22 vinyls per 1000 carbon atoms.

The film may further comprise a low density polyethylene (LDPE). The film may comprise from 5 to 30 wt. %, based on the total weight of polymers present in the film, of a LDPE. All individual values and subranges from 5 to 30 wt. % are included and disclosed herein. For example, in some embodiments, the film may comprise from 10 to 30 wt. %, based on the total weight of polymers present in the film, of a LDPE. In other embodiments, the film may comprise from 10 to 25 wt. %, based on the total weight of polymers present in the film, of a LDPE. In further, embodiments, the film may comprise from 10 to 20 wt. %, based on the total weight of polymers present in the film, of a LDPE.

In embodiments herein, the LDPE present may have a density of about 0.915-0.935 g/cc. All individual values and subranges from 0.915-0.935 g/cc are included and disclosed herein. For example, in some embodiments, the LDPE has a density of 0.915-0.930 g/cc. In other embodiments, the LDPE has a density of 0.915-0.925 g/cc. In embodiments herein, the LDPE may have a melt index, $I_2$, of 0.1-20 g/10 min. All individual values and subranges from 0.1-20 g/10 min are included and disclosed herein. For example, in some embodiments, the LDPE has a melt index, $I_2$, of 0.5 to 20 g/10 min, 0.5 to 18 g/10 min, 0.5 to 16 g/10 min, 0.5 to 14 g/10 min, 0.5 to 12 g/10 min, or 0.5 to 10 g/10 min. In other embodiments, the LDPE has a melt index, $I_2$, of 1 to 20 g/10 min, 1 to 18 g/10 min, 1 to 16 g/10 min, 1 to 14 g/10 min, 1 to 12 g/10 min, or 1 to 10 g/10 min.

The term LDPE may also be used to refer to "high pressure ethylene polymer" or "highly branched polyethylene," and may include branched polymers that are partly or entirely homopolymerized or copolymerized in autoclave or tubular reactors at pressures above 14,500 psi (100 MPa) with the use of free-radical initiators, such as peroxides (see for example U.S. Pat. No. 4,599,392, incorporated herein by reference). Examples of suitable LDPEs may include, but are not limited to, ethylene homopolymers, and high pressure copolymers, including ethylene interpolymerized with, for example, vinyl acetate, ethyl acrylate, butyl acrylate, acrylic acid, methacrylic acid, carbon monoxide, or combinations thereof. Exemplary LDPE resins may include resins sold by The Dow Chemical Company, such as, LDPE 722, LDPE 640I, and LDPE 6211. Other exemplary LDPE resins are described in WO 2005/023912, which is herein incorporated by reference.

The films described herein may further comprise one or more additional polymers, such as polypropylene, propylene-based plastomers or elastomers, ethylene/vinyl alcohol (EVOH) copolymers, polyvinylidene chloride (PVDC), polyethylene terephalate (PET), oriented polypropylene (OPP), ethylene/vinyl acetate (EVA) copolymers, ethylene/acrylic acid (EAA) copolymers, ethylene/methacrylic acid (EMAA) copolymers, polyacrylic imides, butyl acrylates, peroxides (such as peroxypolymers, e.g., peroxyolefins), silanes (e.g., epoxysilanes), reactive polystyrenes, chlorinated polyethylene, olefin block copolymers, propylene copolymers, propylene-ethylene copolymers, ULDPE, LLDPE, HDPE, MDPE, LMDPE, LDPE, ionomers, and graft-modified polymers (e.g., maleic anhydride grafted polyethylene). The one or more additional polymers may be present in an amount of less than 30 wt. %, less than 25 wt. %, less than 20 wt. %, less than 15 wt. %, less than 12 wt. %, less than 10 wt. %, less than 8 wt. %, less than 5 wt. %, less than 3 wt. %, less than 2 wt. %, less than 1 wt. %, or less than 0.5 wt. %, based on the total weight of polymers present in the film.

The films described herein may be made via any number of processes. Exemplary processes may include making the film into a cast film, where the polymer is extruder through a flat die to create a flat film. In some embodiments, the film may be a multilayer film. The multilayer film may be coextruded, whereby a first layer is coextruded to a second layer.

In embodiments herein, the film may have a basis weight of between about 8-30 gsm. All individual values and subranges from 8-30 gsm are included and disclosed herein. For example, in some embodiments, the film may have a basis weight of between about 8-25 gsm. In other embodiments, the film may have a basis weight of between about 8-20 gsm. In further embodiments, the film may have a basis weight of between about 10-20 gsm.

The films described herein are non-breathable. The term "non-breathable" refers to a material which is not permeable to water vapor and has a minimum WVTR (water vapor transmission rate) of less than 500 g/m$^2$/24 hours. In some embodiments, the WVTR is less than about 400 g/m$^2$/24 hours. In other embodiments, the WVTR is less than about 300 g/m$^2$/24 hours. In further embodiments, the WVTR is less than about 200 g/m$^2$/24 hours. In even further embodiments, the WVTR is less than about 100 g/m$^2$/24 hours. In even further embodiments, the WVTR is less than about 50 g/m$^2$/24 hours. A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permanence of the film to water vapor and, for homogeneous materials, water vapor permeability coefficient.

The film may independently comprise one or more additives. The non-breathable films may include fillers, like $CaCO_3$, clay, silica, alumina, titania, zirconia, ceria, talc, magnesium carbonate, calcium sulfate, barium sulfate, porous glass beads, porous polymeric beads, ceramic beads, aluminum trihydroxide, magnesium trihydroxide, wollastonite whiskers, wood flour, lignin, starch, clay, or a combination thereof, in an amount of 0-30 wt. %, 0-25 wt. %, 0-20 wt. %, or 0-15 wt. %, based on the total weight of polymers present in the film. In some embodiments, the fillers may be present in an amount of less than 30 wt. %, less than 25 wt. %, less than 20 wt. %, less than 15 wt. %, less than 14 wt. %, less than 12 wt. %, less than 10 wt. %, less than 8 wt. %, less than 6 wt. %, less than 5 wt. %, less than 4 wt. %, less than 3 wt. %, less than 2 wt. %, less than 1 wt. %, or less than 0.5 wt. %, based on the total weight of polymers present in the film.

Other additives may include, but are not limited to, antioxidants (e.g., hindered phenolics, such as, IRGANOX® 1010 or IRGANOX® 1076, supplied by Ciba Geigy), phosphites (e.g., IRGAFOS® 168, also supplied by Ciba Geigy), cling additives (e.g., PIB (polyisobutylene)), Standostab PEPQ™ (supplied by Sandoz), pigments, colorants, $TiO_2$, anti-stat additives, flame retardants, slip agents, antiblock additives, biocides, antimicrobial agents, and clarifiers/nucleators (e.g., HYPERFORM™ HPN-20E, MILLAD™ 3988, MILLAD™ NX 8000, available from Milliken Chemical). The other additives can be included in the film at levels typically used in the art to achieve their desired purpose. In some examples, the one or more additives are included in amounts ranging from 0-10%, based on total polymer weight of the film, 0-5%, based on total polymer weight of the film, 0.001-5%, based on total polymer weight of the film, 0.001-3%, based on total polymer weight of the film, 0.05-3%, based on total polymer weight of the film, or 0.05-2%, based on total polymer weight of the film.

Laminates

Also described herein are laminates. The laminates comprise a film as previously described herein, and a nonwoven substrate at least partially bonded to the film. As used herein, "nonwoven substrates" include nonwoven webs, nonwoven fabrics and any nonwoven structure in which individual fibers or threads are interlaid, but not in a regular or repeating manner. Nonwoven substrates described herein may be formed by a variety of processes, such as, for example, air laying processes, meltblowing processes, spunbonding processes and carding processes, including bonded carded web processes.

The nonwoven web may comprise a single web, such as a spunbond web, a carded web, an airlaid web, a spunlaced web, or a meltblown web. However, because of the relative strengths and weaknesses associated with the different processes and materials used to make nonwoven fabrics, composite structures of more than one layer are often used in order to achieve a better balance of properties. Such structures are often identified by letters designating the various layers, such as, SM for a two layer structure consisting of a spunbond layer and a meltblown layer, SMS for a three layer structure, or more generically SXnS structures, where S is a spunbond layer, and X can be independently a spunbond layer, a carded layer, an airlaid layer, a spunlaced layer, or a meltblown layer and n can be any number, although for practical purposes is generally less than 5. In order to maintain structural integrity of such composite structures, the layers must be bonded together. Common methods of bonding include thermal calendar point bonding, adhesive lamination, ultrasonic bonding, and other methods known to those skilled in the art. All of these structures may be used in the present invention.

Articles

Also described herein are articles. The articles comprise a film or a laminate as previously described herein. The articles may be used in a variety of hygiene and medical applications. In some embodiments, the articles may include diapers, training pants, and adult incontinence articles, or other similar absorbent garment article. In other embodiments, the articles may include medical drapes, gowns, and surgical suits, or in other fabric (woven or nonwoven) articles.

Test Methods

Density

Density can be measured in accordance with ASTM D-792.

Melt Index

Melt index ($I_2$) can be measured in accordance with ASTM D-1238, Procedure B (condition 190° C./2.16 kg). Melt index ($I_{10}$) can be measured in accordance with ASTM D-1238, Procedure B (condition 190° C./10.0 kg).

Gel Permeation Chromatography (GPC)

The chromatographic system consisted of a PolymerChar GPC-IR (Valencia, Spain) high temperature GPC chromatograph equipped with an internal IR5 detector. The autosampler oven compartment was set at 160° Celsius and the column compartment was set at 150° Celsius. The columns used were 3 Agilent "Mixed B" 30 cm 10-micron linear mixed-bed columns and a 10-μm pre-column. The chromatographic solvent used was 1,2,4 trichlorobenzene and contained 200 ppm of butylated hydroxytoluene (BHT). The solvent source was nitrogen sparged. The injection volume used was 200 microliters and the flow rate was 1.0 milliliters/minute.

Calibration of the GPC column set was performed with 21 narrow molecular weight distribution polystyrene standards with molecular weights ranging from 580 to 8,400,000 and were arranged in 6 "cocktail" mixtures with at least a decade of separation between individual molecular weights. The standards were purchased from Agilent Technologies. The polystyrene standards were prepared at 0.025 grams in 50 milliliters of solvent for molecular weights equal to or greater than 1,000,000, and 0.05 grams in 50 milliliters of solvent for molecular weights less than 1,000,000. The polystyrene standards were dissolved at 80 degrees Celsius with gentle agitation for 30 minutes. The polystyrene standard peak molecular weights were converted to polyethylene molecular weights using Equation 1 (as described in Williams and Ward, J. Polym. Sci., Polym. Let., 6, 621 (1968)):

$$M_{polyethylene} = A \times (M_{polystyrene})^B \quad \text{(EQ1)}$$

where M is the molecular weight, A has a value of 0.4315 and B is equal to 1.0.

A fifth order polynomial was used to fit the respective polyethylene-equivalent calibration points. A small adjustment to A (from approximately 0.415 to 0.44) was made to correct for column resolution and band-broadening effects such that NIST standard NBS 1475 is obtained at 52,000 g/mol Mw.

The total plate count of the GPC column set was performed with Eicosane (prepared at 0.04 g in 50 milliliters of TCB and dissolved for 20 minutes with gentle agitation.) The plate count (Equation 2) and symmetry (Equation 3) was measured on a 200 microliter injection according to the following equations:

$$\text{Plate Count} = 5.54 * \left( \frac{RV_{Peak\ Max}}{\text{Peak Width at } \frac{1}{2} \text{ height}} \right)^2 \quad \text{(EQ 2)}$$

where RV is the retention volume in milliliters, the peak width is in milliliters, the peak max is the maximum height of the peak, and ½ height is ½ height of the peak maximum.

$$\text{Symmetry} = \frac{(\text{Rear Peak } RV_{one\ tenth\ height} - RV_{Peak\ max})}{(RV_{Peak\ max} - \text{Front Peak } RV_{one\ tenth\ height})} \quad \text{(EQ 3)}$$

where RV is the retention volume in milliliters and the peak width is in milliliters, peak max is the maximum position of the peak, one tenth height is ¹/₁₀ height of the peak maximum, rear peak refers to the peak tail at later retention volumes than the peak max, and front peak refers to the peak front at earlier retention volumes than the peak max. The plate count for the chromatographic system should be greater than 24,000 and symmetry should be between 0.98 and 1.22.

Samples were prepared in a semi-automatic manner with the PolymerChar "Instrument Control" Software, wherein the samples were weight-targeted at 2 mg/ml, and the solvent (contained 200 ppm BHT) was added to a pre nitrogen-sparged septa-capped vial, via the PolymerChar high temperature autosampler. The samples were dissolved for 2 hours at 160° Celsius under "low speed" shaking.

The calculations of Mn, Mw, and Mz were based on GPC results using the internal IR5 detector (measurement channel) of the PolymerChar GPC-IR chromatograph according to Equations 4-6, using PolymerChar GPCOne™ software, the baseline-subtracted IR chromatogram at each equally-spaced data collection point (i), and the polyethylene equivalent molecular weight obtained from the narrow standard calibration curve for the point (i) from Equation 1.

$$M_n = \frac{\sum_i IR_i}{\sum_i \left(\frac{IR_i}{M_{polyethylene_i}}\right)} \quad (EQ\ 4)$$

$$M_w = \frac{\sum_i (IR_i * M_{polyethylene_i})}{\sum_i IR_i} \quad (EQ\ 5)$$

$$M_z = \frac{\sum_i (IR_i * M_{polyethylene_i}^2)}{\sum_i (IR_i * M_{polyethylene_i})} \quad (EQ\ 6)$$

In order to monitor the deviations over time, a flowrate marker (decane) was introduced into each sample via a micropump controlled with the PolymerChar GPC-IR system. This flowrate marker was used to linearly correct the flowrate for each sample by alignment of the respective decane peak within the sample to that of the decane peak within the narrow standards calibration. Any changes in the time of the decane marker peak are then assumed to be related to a linear shift in both flowrate and chromatographic slope. To facilitate the highest accuracy of a RV measurement of the flow marker peak, a least-squares fitting routine is used to fit the peak of the flow marker concentration chromatogram to a quadratic equation. The first derivative of the quadratic equation is then used to solve for the true peak position. After calibrating the system based on a flow marker peak, the effective flowrate (as a measurement of the calibration slope) is calculated as Equation 7. Processing of the flow marker peak was done via the PolymerChar GPCOne™ Software.

$$Flowrate_{effective} = Flowrate_{nominal} \times \frac{FlowMarker_{Calibration}}{FlowMarker_{Observed}} \quad (EQ\ 7)$$

Neutron Activation Method for Metals

Two sets of duplicate samples were prepared by transferring approximately 3.5 grams of the pellets into pre-cleaned 2 dram polyethylene vials. Standards were prepared for each metal tested from their NIST traceable standard solutions (Certi. pure from SPEX) into 2-dram polyethylene vials. They were diluted using milli-Q pure water to 6 ml and the vials were heat-sealed. The samples and standards were then analyzed for these elements, using a Mark I TRIGA nuclear reactor. The reactions and experimental conditions used for these elements are summarized in the table below. The samples were transferred to un-irradiated vials before doing the gamma-spectroscopy. The elemental concentrations were calculated using CANBERRA software and standard comparative technique. Table 1 provides measurement parameters for metals determination.

TABLE 1

Reactions and experimental conditions used for elements during the neutron activation method

| Elements | Nuclear reaction | Isotope | Half life | Reactor Power |
| --- | --- | --- | --- | --- |
| Al | $^{27}Al(n,\gamma)^{28}Al$ | $^{28}Al$ | 2.24 m | 250 kW |
| Cl | $^{37}Cl(n,\gamma)^{38}Cl$ | $^{38}Cl$ | 37.2 m | 250 kW |
| Cr | $^{50}Cr(n,\gamma)^{51}Cr$ | $^{51}Cr$ | 27.7 d | 250 kW |
| Hf | $^{180}Hf(n,\gamma)^{181}Hf$ | $^{181}Hf$ | 42.4 d | 250 kW |
| Mg | $^{26}Mg(n,\gamma)^{27}Mg$ | $^{27}Mg$ | 9.46 m | 250 kW |
| Mo | $^{98}Mo(n,\gamma)^{99}Mo$ | $^{99}Mo$ | 66.0 h | 250 kW |
| Nb | $^{93}Nb(n,\gamma)^{94m}Nb$ | $^{94m}Nb$ | 6.26 m | 250 kW |
| Ta | $^{181}Ta(n,\gamma)^{182}Ta$ | $^{182}Ta$ | 114.4 d | 250 kW |
| Ti | $^{50}Ti(n,\gamma)^{51}Ti$ | $^{51}Ti$ | 5.76 m | 250 kW |
| W | $^{186}W(n,\gamma)^{187}W$ | $^{187}W$ | 23.7 h | 250 kW |
| V | $^{51}V(n,\gamma)^{52}V$ | $^{52}V$ | 3.75 m | 250 kW |
| Zr | $^{96}Zr(n,\gamma)^{97}Zr$ | $^{97}Zr$ | 16.91 h | 250 kW |

| Elements | Irradiation Time | Waiting Time | Counting Time | Gamma Energy, keV |
| --- | --- | --- | --- | --- |
| Al | 2 m | 4 m | 4.5 min | 1778.5 |
| Cl | 2 m | 4 m | 4.5 min | 1642.5, 2166.5 |
| Cr | 90 m | 5 h | 1.6 h | 320 |
| Hf | 90 m | 5 h | 1.6 h | 133, 482 |
| Mg | 2 m | 4 m | 4.5 min | 843.8, 1014 |
| Mo | 90 m | 5 h | 1.6 h | 181, 739.7, 141 |
| Nb | 2 m | 4 m | 4.5 min | 871 |
| Ta | 90 m | 5 h | 1.6 h | 1121, 1222 |
| Ti | 2 m | 4 m | 4.5 min | 320 |
| W | 90 m | 5 h | 1.6 h | 135, 481 |
| V | 2 m | 4 m | 4.5 min | 1434 |
| Zr | 90 m | 5 h | 1.6 h | 743.4 |

Differential Scanning calorimetry (DSC)

DSC was used to measure the melting and crystallization behavior of a polymer over a wide range of temperatures. For example, the TA Instruments Q1000 DSC, equipped with an RCS (refrigerated cooling system) and an autosampler was used to perform this analysis. During testing, a nitrogen purge gas flow of 50 ml/min was used. Each sample was melt pressed into a thin film at about 175° C.; the melted sample was then air-cooled to room temperature (approx. 25° C.). The film sample was formed by pressing a "0.1 to 0.2 gram" sample at 175° C. at 1,500 psi, and 30 seconds, to form a "0.1 to 0.2 mil thick" film. A 3-10 mg, 6 mm diameter specimen was extracted from the cooled polymer, weighed, placed in a light aluminum pan (ca 50 mg), and crimped shut. Analysis was then performed to determine its thermal properties.

The thermal behavior of the sample was determined by ramping the sample temperature up and down to create a heat flow versus temperature profile. First, the sample was rapidly heated to 180° C., and held isothermal for five minutes, in order to remove its thermal history. Next, the sample was cooled to −40° C., at a 10° C./minute cooling rate, and held isothermal at −40° C. for five minutes. The sample was then heated to 150° C. (this is the "second heat" ramp) at a 10° C./minute heating rate. The cooling and second heating curves were recorded. The cool curve was analyzed by setting baseline endpoints from the beginning of crystallization to −20° C. The heat curve was analyzed by setting baseline endpoints from −20° C. to the end of melt. The values determined were peak melting temperature ($T_m$), peak crystallization temperature ($T_c$), heat of fusion ($H_f$) (in Joules per gram), and the calculated % crystallinity for polyethylene samples using: % Crystallinity=(($H_f$)/(292 J/g))×100. The heat of fusion ($H_f$) and the peak melting temperature were reported from the second heat curve. Peak crystallization temperature is determined from the cooling curve.

Melt Strength

Melt strength was measured at 190° C. using a Göettfert Rheotens 71.97 (Göettfert Inc.; Rock Hill, S.C.), melt fed with a Göettfert Rheotester 2000 capillary rheometer equipped with a flat entrance angle (180 degrees) of length of 30 mm and diameter of 2.0 mm. The pellets (20-30 gram pellets) were fed into the barrel (length=300 mm, diameter=12 mm), compressed and allowed to melt for 10 minutes before being extruded at a constant piston speed of 0.265 mm/s, which corresponds to a wall shear rate of 38.2 $s^{-1}$ at the given die diameter. The extrudate passed through the wheels of the Rheotens located 100 mm below the die exit and was pulled by the wheels downward at an acceleration rate of 2.4 $mm/s^2$. The force (in cN) exerted on the wheels was recorded as a function of the velocity of the wheels (in mm/s). Melt strength is reported as the plateau force (cN) before the strand broke.

Dynamic Mechanical Spectroscopy (DMS)

Resins were compression-molded into "3 mm thick×1 inch diameter" circular plaques at 350° F., for five minutes, under 1500 psi pressure, in air. The sample was then taken out of the press, and placed on a counter to cool.

A constant temperature frequency sweep was performed using a TA Instruments "Advanced Rheometric Expansion System (ARES)," equipped with 25 mm (diameter) parallel plates, under a nitrogen purge. The sample was placed on the plate, and allowed to melt for five minutes at 190° C. The plates were then closed to a gap of "2 mm," the sample trimmed (extra sample that extends beyond the circumference of the "25 mm diameter" plate was removed), and then the test was started. The method had an additional five minute delay built in, to allow for temperature equilibrium. The experiments were performed at 190° C. over a frequency range of 0.1 to 100 rad/s. The shear strain amplitude was constant at 10%. The complex viscosity $\eta^*$, tan ($\delta$) or tan delta, viscosity at 0.1 rad/s (V0.1), the viscosity at 100 rad/s (V100), and the viscosity ratio (V0.1/V100) were calculated from these data.

Crystallization Elution Fractionation (CEF) Method

The Crystallization Elution Fractionation (CEF) technology is conducted according to Monrabal et al, Macromol. Symp. 257, 71-79 (2007). The CEF instrument is equipped with an IR-4 or IR-5 detector (such as that sold commercially from PolymerChar, Spain) and a two angle light scattering detector Model 2040 (such as those sold commercially from Precision Detectors). A 10 micron guard column of 50 mm×4.6 mm (such as that sold commercially from PolymerLabs) is installed before the IR-4 or IR-5 detector in the detector oven. Ortho-dichlorobenzene (ODCB, 99% anhydrous grade) and 2,5-di-tert-butyl-4-methylphenol (BHT) (such as commercially available from Sigma-Aldrich) are obtained. Silica gel 40 (particle size 0.2-0.5 mm) (such as commercially available from EMD Chemicals) is also obtained. The silica gel is dried in a vacuum oven at 160° C. for at least two hours before use. ODCB is sparged with dried nitrogen ($N_2$) for one hour before use. Dried nitrogen is obtained by passing nitrogen at <90 psig over $CaCO_3$ and 5 Å molecular sieves. ODCB is further dried by adding five grams of the dried silica to two liters of ODCB or by pumping through a column or columns packed with dried silica between 0.1 ml/min to 1.0 ml/min. Eight hundred milligrams of BHT are added to two liters of ODCB if no inert gas such as $N_2$ is used in purging the sample vial. Dried ODCB with or without BHT is hereinafter referred to as "ODCB-m." A sample solution is prepared by, using the autosampler, dissolving a polymer sample in ODCB-m at 4 mg/ml under shaking at 160° C. for 2 hours. 300 μL of the sample solution is injected into the column. The temperature profile of CEF is: crystallization at 3° C./min from 110° C. to 30° C., thermal equilibrium at 30° C. for 5 minutes (including Soluble Fraction Elution Time being set as 2 minutes), and elution at 3° C./min from 30° C. to 140° C. The flow rate during crystallization is 0.052 ml/min. The flow rate during elution is 0.50 ml/min. The IR-4 or IR-5 signal data is collected at one data point/second.

The CEF column is packed with glass beads at 125 μm±6% (such as those commercially available with acid wash from MO-SCI Specialty Products) with ⅛ inch stainless tubing according to U.S. Pat. No. 8,372,931. The internal liquid volume of the CEF column is between 2.1 ml and 2.3 ml. Temperature calibration is performed by using a mixture of NIST Standard Reference Material linear polyethylene 1475a (1.0 mg/ml) and Eicosane (2 mg/ml) in ODCB-m. The calibration consists of four steps: (1) calculating the delay volume defined as the temperature offset between the measured peak elution temperature of Eicosane minus 30.00° C.; (2) subtracting the temperature offset of the elution temperature from the CEF raw temperature data. It is noted that this temperature offset is a function of experimental conditions, such as elution temperature, elution flow rate, etc.; (3) creating a linear calibration line transforming the elution temperature across a range of 30.00° C. and 140.00° C. such that NIST linear polyethylene 1475a has a peak temperature at 101.00° C., and Eicosane has a peak temperature of 30.00° C., (4) for the soluble fraction measured isothermally at 30° C., the elution temperature is extrapolated linearly by using the elution heating rate of 3° C./min. The reported elution peak temperatures are obtained such that the observed comonomer content calibration curve agrees with those previously reported in U.S. Pat. No. 8,372,931.

The CEF chromatogram is divided into zones, the elution temperature range of each zone is specified in Table 6. In this case, the wt % of the lowest temperature zone is called the wt % of Zone 1 or the wt % of the purge fraction. The wt % of the highest temperature zone or Zone 2 is the wt % of the high density fraction.

Comonomer Distribution Breadth Index (CDBI)

The CDBI is calculated using the methodology described in WO/93/03093 from data obtained from CEF. CDBI is defined as the weight percent of the polymer molecules having a comonomer content within 50 percent of the median total molar comonomer content. It represents a comparison of the comonomer distribution in the polymer to the comonomer distribution expected for a Bernoullian distribution.

CEF is used to measure the short chain branching distribution (SCBD) of the polyolefin. A CEF molar comonomer content calibration is performed using 24 reference materials (e.g., polyethylene octene random copolymer and ethylene butene copolymer) with a narrow SCBD having a comonomer mole fraction ranging from 0 to 0.108 and a Mw from 28,400 to 174,000 g/mole. The ln (mole fraction of ethylene), which is the ln (comonomer mole fraction), versus 1/T (K) obtained, where T is the elution temperature in Kelvin of each reference material. The comonomer distribution of the reference materials is determined using 13C NMR analysis in accordance with techniques described, for example, in U.S. Pat. No. 5,292,845 (Kawasaki, et al.) and by J. C. Randall in Rev. Macromol. Chem. Phys., C29, 201-317.

Nuclear Magnetic Resonance ($^1$H NMR)

The samples were prepared by adding approximately 130 mg of sample to "3.25 g of 50/50, by weight, tetrachlorethane-$d_2$/perchloroethylene (TCE-$d_2$)" with 0.001 M Cr(AcAc)$_3$ in a NORELL 1001-7, 10 mm NMR tube. The samples were purged by bubbling $N_2$ through the solvent, via a pipette inserted into the tube, for approximately five minutes, to prevent oxidation. Each tube was capped, sealed with TEFLON tape, and then soaked at room temperature, overnight, to facilitate sample dissolution. The samples were heated and vortexed at 115° C. to ensure homogeneity.

The $^1$H NMR was performed on a Bruker AVANCE 400 MHz spectrometer, equipped with a Bruker Dual DUL high-temperature CryoProbe, and a sample temperature of 120° C. Two experiments were run to obtain spectra, a control spectrum to quantitate the total polymer protons, and a double presaturation experiment, which suppressed the intense polymer backbone peaks, and enabled high sensitivity spectra for quantitation of the end-groups. The control was run with ZG pulse, 16 scans, AQ 1.64 s, D1 14 s. The double presaturation experiment was run with a modified pulse sequence, 100 scans, AQ 1.64 s, presaturation delay 1 s, relaxation delay 13 s.

The signal from residual $^1$H in TCE-$d_2$ (at 6.0 ppm) was integrated, and set to a value of 100, and the integral from 3 to −0.5 ppm was used as the signal from the whole polymer in the control experiment. For the presaturation experiment, the TCE signal was also set to 100, and the corresponding integrals for unsaturation (vinylene at about 5.40 to 5.60 ppm, trisubstituted at about 5.16 to 5.35 ppm, vinyl at about 4.95 to 5.15 ppm, and vinylidene at about 4.70 to 4.90 ppm) were obtained.

In the presaturation experiment spectrum, the regions for cis- and trans-vinylene, trisubstituted, vinyl, and vinylidene were integrated. The integral of the whole polymer from the control experiment was divided by two to obtain a value representing X thousands of carbons (i.e., if the polymer integral=28000, this represents 14,000 carbons, and X=14).

The unsaturated group integrals, divided by the corresponding number of protons contributing to that integral, represent the moles of each type of unsaturation per X thousand carbons. Dividing the moles of each type of unsaturation by X, then gives moles unsaturated groups per 1000 moles of carbons.

Film Property Test Methods

Spencer Dart Impact

Spencer dart impact testing is conducted following ASTM D3420 methodology, using 10 specimens per sample.

Puncture

Puncture is measured using ASTM D5748, except that the probe used is 0.5" in diameter and is stainless steel. Speed=250 mm/min.

Force to Draw

Force to draw is measured according to ASTM D 882, for films less than 1 mm (0.04 in) in thickness. Film samples are cut into 1 inch wide strips by 4 inch length, and pulled at 2 inches/min speed. Values for stress at 1 and 2% strain were reported.

Elmendorf Tear

Elmendorf tear test data is measured on all films in accordance with ASTM D1922-09. All samples are tested in the machine direction (MD) and the cross-direction (CD). 15 specimens per each sample are tested and the average value is recorded.

Stress and Strain at Break

Stress-Strain behavior in uniaxial tension is measured according with ASTM D-638. Samples of dimensions 1 inch width by 2 inch length are cut from the films and stretched with an Instron at 20 inches/min at 23° C. Engineering tensile strengths/stress at break and strain at break are reported for an average of 5 specimens.

EXAMPLES

A multi-metal catalyst is prepared (Catalyst 1) and a non-multi-metal catalyst is prepared (Catalyst A). Catalyst 1 is then used to prepare inventive polyethylene compositions in a solution polymerization. Catalyst A is used to prepare comparative polyethylene compositions. Subsequently, the inventive and comparative polyethylene compositions are used to prepare inventive and comparative cast films, respectively. Testing is carried out on both the polyethylene compositions and the cast films.

General Description of Preparation of Catalysts

The catalyst compositions may be prepared beginning first with preparation of a conditioned magnesium halide based support. Preparation of a conditioned magnesium halide based support begins with selecting an organomagnesium compound or a complex including an organomagnesium compound. Such compound or complex is desirably soluble in an inert hydrocarbon diluent. In one embodiment, the concentrations of components are such that when the active halide, such as a metallic or non-metallic halide, and the magnesium complex are combined, the resultant slurry is from about 0.005 to about 0.3 molar (moles/liter) with respect to magnesium. Examples of suitable inert organic diluents include liquefied ethane, propane, isobutane, n-butane, n-hexane, the various isomeric hexanes, isooctane, paraffinic mixtures of alkanes having from 5 to 10 carbon atoms, cyclohexane, methylcyclopentane, dimethylcyclohexane, dodecane, industrial solvents composed of saturated or aromatic hydrocarbons such as kerosene, naphthas, and combinations thereof, especially when freed of any olefin compounds and other impurities, and especially those having boiling points in the range from about −50° C. to about 200° C. Also included as suitable inert diluents are ethylbenzene, cumene, decalin and combinations thereof.

Suitable organomagnesium compounds and complexes may include, for example, magnesium C2-C8 alkyls and aryls, magnesium alkoxides and aryloxides, carboxylated magnesium alkoxides, and carboxylated magnesium aryloxides. Preferred sources of magnesium moieties may include the magnesium C2-C8 alkyls and C1-C4 alkoxides. Such organomagnesium compound or complex may be reacted with a metallic or non-metallic halide source, such as a chloride, bromide, iodide, or fluoride, in order to make a magnesium halide compound under suitable conditions. Such conditions may include a temperature ranging from −25° C. to 100° C., or alternatively, 0° C. to 50° C.; a time ranging from 1 to 12 hours, or alternatively, from 4 to 6 hours; or both. The result is a magnesium halide-based support.

The magnesium halide support is then reacted with a selected conditioning compound containing an element selected from the group consisting of boron, aluminum, gallium, indium and tellurium, under conditions suitable to form a conditioned magnesium halide support. This compound and the magnesium halide support are then brought into contact under conditions sufficient to result in a conditioned magnesium halide support. Such conditions may include a temperature ranging from 0° C. to 50° C., or alternatively, from 25° C. to 35° C.; a time ranging from 4 to 24 hours, or alternatively, from 6 to 12 hours; or both. Without wishing to be bound by any theory of mechanism, it is suggested that this aging serves to facilitate or enhance adsorption of additional metals onto the support.

Once the conditioned support is prepared and suitably aged, it is brought into contact with a titanium compound. In certain preferred embodiments titanium halides or alkoxides, or combinations thereof, may be selected. Conditions may include a temperature within the range from 0° C. to 50° C., or alternatively, from 25° C. to 35° C.; a time from 3 hours to 24 hours, or alternatively, from 6 hours to 12 hours; or both. The result of this step is adsorption of at least a portion of the titanium compound onto the conditioned magnesium halide support.

Additional Steps in Preparing Multi-Metal Catalyst Used to Make the Inventive Polyethylene Compositions For those catalysts used to make the inventive polyethylene compositions, i.e. multi-metal catalysts herein, two additional metals, referred to herein as "the second metal" and "the third metal" for convenience, will also be adsorbed onto the magnesium based support, The "second metal" and the "third metal" are independently selected from zirconium (Zr), hafnium (Hf), vanadium (V), niobium (Nb), tantalum (Ta), chromium (Cr), molybdenum (Mo), and tungsten (W). These metals may be incorporated in any of a variety of ways known to those skilled in the art, but generally contact between the conditioned magnesium based halide support including titanium and the selected second and third metals, in, e.g., liquid phase such as an appropriate hydrocarbon solvent, will be suitable to ensure deposition of the additional metals to form what may now be referred to as the "procatalyst," which is a multi-metallic procatalyst.

In certain embodiments, the multi-metal procatalyst exhibits a molar ratio of the magnesium to a combination of the titanium and the second and third metals that ranges from 30:1 to 5:1; under conditions sufficient to form a multi-metallic procatalyst. Thus, the overall molar ratio of magnesium to titanium ranges from 8:1 to 80:1.

Once the procatalyst has been formed, it may be used to form a final catalyst by combining it with a cocatalyst consisting of at least one organometallic compound such as an alkyl or haloalkyl of aluminum, an alkylaluminum halide, a Grignard reagent, an alkali metal aluminum hydride, an alkali metal borohydride, an alkali metal hydride, an alkaline earth metal hydride, or the like. The formation of the final catalyst from the reaction of the procatalyst and the organometallic cocatalyst may be carried out in situ, or just prior to entering the polymerization reactor. Thus, the combination of the cocatalyst and the procatalyst may occur under a wide variety of conditions. Such conditions may include, for example, contacting them under an inert atmosphere such as nitrogen, argon or other inert gas at temperatures in the range from 0° C. to 250° C., or alternatively, from 15° C. to 200° C. In the preparation of the catalytic reaction product, it is not necessary to separate hydrocarbon soluble components from hydrocarbon insoluble components. Time for contact between the procatalyst and cocatalyst may range, for example, from 0 to 240 seconds, or alternatively, from 5 to 120 seconds. Various combinations of these conditions may be employed.

Catalyst A Preparation

To 800 mL of $MgCl_2$ (0.20 M in ISOPAR™ E) is added $(C_2H_5)AlCl_2$ (EADC) (48 mL of a 1.0 M solution in hexane). The resulting mixture is allowed to stir overnight at room temperature. A solution of $Ti(OiPr)_4$ (titanium isopropoxide, 48 mL of a 0.25 M solution in ISOPAR™ E) is then added to the magnesium/aluminum suspension. The resulting mixture is allowed to stir overnight to complete the procatalyst aging.

Catalyst 1 Preparation

To approximately 109 kg of 0.20 M $MgCl_2$ slurry was added 7.76 kg of $(C_2H_5)AlCl_2$ (EADC) solution (15 wt. % in heptanes), followed by agitation for 8 hours. A mixture of $TiCl_4$/$VOCl_3$ (85 mL and 146 mL, respectively) was then added, followed by a solution of $Zr(TMHD)_4$ (Zirconium tetrakis(2,2,6,6-tetramethyl-3,5-heptanedionate) (0.320 kg of a 0.30 M solution in Isopar E). These two additions were performed sequentially within 1 hour of each other. The resulting catalyst premix was aged with agitation for an additional 8 h prior to use.

Each of the catalysts prepared hereinabove is then used to prepare Polyethylene Compositions as described below.

Production of Inventive Polyethylene Composition Examples 1 and 2 and Comparative Polyethylene Composition Example B All raw materials (monomer and comonomer) and the process solvent (a narrow boiling range high-purity isoparaffinic solvent) are purified with molecular sieves before introduction into the reaction environment. Hydrogen is supplied in pressurized cylinders as a high purity grade and is not further purified. The reactor monomer feed stream is pressurized via a mechanical compressor to above reaction pressure. The solvent and comonomer feed is pressurized via a pump to above reaction pressure. The individual catalyst components are manually batch diluted to specified component concentrations with purified solvent and pressured to above reaction pressure. All reaction feed flows are measured with mass flow meters and independently controlled with computer automated valve control systems.

The fresh comonomer feed is mechanically pressurized and can be injected into the process at several potential locations depending on reactor configuration which include: only the feed stream for the first/single reactor. Reactor configuration is single reactor operation.

The continuous solution polymerization reactor consists of a liquid full, non-adiabatic, isothermal, circulating, loop reactor which mimics a continuously stirred tank reactor (CSTR) with heat removal. Independent control of all fresh solvent, monomer, comonomer, hydrogen, and catalyst component feeds is possible. The total fresh feed stream to the reactor (solvent, monomer, comonomer, and hydrogen) is temperature controlled by passing the feed stream through a heat exchanger. The total fresh feed to the polymerization reactor is injected into the reactor at two locations with approximately equal reactor volumes between each injection location. The fresh feed is controlled with each injector receiving half of the total fresh feed mass flow. The catalyst components are injected into the polymerization reactor through a specially designed injection stinger and are combined into one mixed catalyst/cocatalyst feed stream prior to injection into the reactor. The primary catalyst component feed is computer controlled to maintain the reactor monomer concentration at a specified target. The cocatalyst component(s) is/are fed based on calculated specified molar ratios to the primary catalyst component. Immediately following each fresh injection location (either feed or catalyst), the feed streams are mixed with the circulating polymerization reactor contents with static mixing elements. The contents of the reactor are continuously circulated through heat exchangers responsible for removing much of the heat of reaction and with the temperature of the coolant side responsible for maintaining an isothermal reaction environment at the specified temperature. Circulation around the reactor loop is provided by a pump.

The final reactor effluent enters a zone where it is deactivated with the addition of and reaction with a suitable reagent (typically water). At this same reactor exit location other additives may also be added.

Following catalyst deactivation and additive addition, the reactor effluent enters a devolatization system where the polymer is removed from the non-polymer stream. The isolated polymer melt is pelletized and collected. The non-polymer stream passes through various pieces of equipment which separate most of the ethylene which is removed from the system. Most of the solvent and unreacted comonomer is recycled back to the reactor after passing through a purification system. A small amount of solvent and comonomer is purged from the process.

Table 2 summarizes the polymerization conditions for Inventive Polyethylene Compositions 1 and 2 (IE 1 and IE 2, respectively) and Comparative Polyethylene Composition B (Comp. B). Additives used in these polymerizations were 700 ppm calcium stearate, 1200 ppm IRGAFOS 168 (which is tris (2,4 di-tert-butylphenyl) phosphite), 250 ppm IRGANOX 1076 (which is octadecyl-3-(3,5-di-tert-butyl-4-hydroxyphenyl)propionate)), and 200 ppm Cyanox 1790 (which is 1,3,5,tris(4-tert-butyl-3-hydroxy-2,6,dimethyl benzyl)-1,3,5-triazine-2,4,6-(1H,3H,5H)-trione)).

IRGAFOS 168 and IRGANOX 1076 are commercially available from BASF. Cyanox 1790 is available from CYTEC industries. Comparative Polyethylene Composition A (Comp. A) is AGILITY™ 6047, available from The Dow Chemical Company.

TABLE 2

Polymerization Conditions

| | | Sample | | |
|---|---|---|---|---|
| | | IE 1 | IE 2 | Comp. B |
| Reactor Configuration | | Single | Single | Single |
| Comonomer Type | | None | 1-octene | 1-octene |
| Reactor Feed Temperature | ° C. | 55 | 40 | 40 |
| Reactor Feed Total Solvent Flow | lb/hr | 1,955 | 1,305 | 1,305 |
| Reactor Feed Total Ethylene Flow | lb/hr | 489 | 485 | 485 |
| Reactor Feed Total Comonomer Flow | lb/hr | 0.00 | 28.34 | 38.52 |
| Reactor Feed Fresh Hydrogen Flow | SCCM | 12,528 | 7,617 | 8,463 |
| Reactor Temperature | ° C. | 185 | 194 | 200 |
| Reactor Pressure | psig | 725 | 725 | 725 |
| Reactor Ethylene Concentration | g/L | 9.4 | 12.9 | 13.1 |
| Reactor Solution Density | lb/ft³ | 37.6 | 37.5 | 37.2 |
| Reactor Viscosity | centipoise | 191 | 1006 | 999 |
| Catalyst Type | Type | Catalyst-1 | Catalyst-1 | Catalyst-A |
| Cocatalyst Type | Type | TEA* | TEA | TEA |
| Cocatalyst Molar Ratio (Al to Ti) | Ratio | 12.2 | 8.5 | 4.0 |
| Catalyst (Ti) Efficiency | g Poly/g Ti | 1,040,370 | 1,285,555 | 866,943 |

*TEA is tri-ethyl-aluminum.

TABLE 3

Measured Melt Index and Density Data

| Sample | $I_2$, g/10 min | $I_{10}/I_2$ | Density (g/cc) |
|---|---|---|---|
| IE 1 | 6.52 | 6.33 | 0.9621 |
| IE 2 | 3.79 | 6.27 | 0.9471 |
| Comp. A | 5.85 | 6.84 | 0.9470 |
| Comp. B | 3.53 | 7.02 | 0.9465 |

TABLE 4

Conventional GPC Data

| Type | Mn (g/mol) | Mw (g/mol) | Mz (g/mol) | Mw/Mn | Mz/Mw | Mz/Mn |
|---|---|---|---|---|---|---|
| IE 1 | 26,470 | 75,468 | 200,781 | 2.85 | 2.66 | 7.59 |
| IE 2 | 30,402 | 86,031 | 228,985 | 2.83 | 2.66 | 7.53 |
| Comp. A | 24,284 | 77,492 | 237,728 | 3.19 | 3.07 | 9.79 |
| Comp. B | 25,935 | 90,548 | 288,199 | 3.49 | 3.18 | 11.11 |

TABLE 5

Melt Strength Data

| Sample | Velocity at Break (mm/s) | Melt Strength (cN) |
|---|---|---|
| IE 1 | 364 | 0.5 |
| IE 2 | 393 | 1.3 |
| Comp. A | 363 | 0.6 |
| Comp. B | 343 | 1.3 |

TABLE 6

CEF and CDBI Data

| Sample | Peak Temperature Range of Each Zone (° C.) Zone 1 | Peak Temperature Range of Each Zone (° C.) Zone 2 | Peak Temperature of Each Zone (° C.) Zone 1 | Peak Temperature of Each Zone (° C.) Zone 2 | Wt % of Each zone Zone 1 | Wt % of Each zone Zone 2 | CDBI |
|---|---|---|---|---|---|---|---|
| IE 1 | 25.05 to 34.47 | 34.57 to 119.96 | 29.95 | 102.41 | 0.51 | 99.49 | 100% |
| IE 2 | 25.05 to 34.46 | 34.56 to 119.97 | 30.00 | 100.24 | 0.42 | 99.58 | 100% |
| Comp. A | 25.05 to 34.49 | 34.58 to 120.00 | 29.81 | 99.44 | 0.49 | 99.51 | 100% |
| Comp. B | 25.04 to 34.46 | 34.56 to 119.97 | 30.02 | 99.79 | 0.50 | 99.50 | 100% |

TABLE 7

DMS Rheology Data (at 190° C.)

| Type | Viscosity (Pa-s at 190° C.) 0.1 rad/s | 1 rad/s | 10 rad/s | 100 rad/s | Viscosity Ratio Viscosity 0.1 rad/s / Viscosity 100 rad/s | Tan Delta 0.1 rad/s |
|---|---|---|---|---|---|---|
| IE 1 | 1,193 | 1,147 | 993 | 635 | 1.9 | 62.1 |
| IE 2 | 2,005 | 1,899 | 1,580 | 920 | 2.2 | 42.8 |
| Comp. A | 1,389 | 1,298 | 1,057 | 614 | 2.3 | 32.4 |
| Comp. B | 2,333 | 2,141 | 1,643 | 853 | 2.7 | 27.9 |

TABLE 8

DSC Data

| Type | $T_m$ (° C.) | Heat of Fusion (J/g) | % Cryst. | $T_c$ (° C.) |
|---|---|---|---|---|
| IE 1 | 134.3 | 231.5 | 79.3 | 117.0 |
| IE 2 | 130.0 | 202.7 | 69.4 | 115.7 |
| Comp. A | 128.3 | 199.6 | 68.4 | 114.5 |
| Comp. B | 128.6 | 200.5 | 68.7 | 114.8 |

TABLE 9

Neutron Activation Data*

| Type | Al, ppm | Mg, ppm | Ti, ppm | V, ppm | Hf, ppb | Zr, ppm | Cl, ppm |
|---|---|---|---|---|---|---|---|
| IE 1 | 11 | 22 | 0.80 | 2.1 | 65 | 0.95 | 69 |
| IE 2 | 7.4 | 13 | 0.39 | 1.2 | ND @ 10 | 0.58 | 45 |
| Comp. A | 73 | 142 | 1.9 | ND @ 0.01 | ND @ 10 | ND @ 0.2 | 67 |
| Comp. B | 4.4 | 9.0 | 0.78 | ND @ 0.01 | ND @ 10 | ND@ 0.2 | 23 |

*Niobium (Nb) (5 ppm), tantalum (Ta) (50 ppb), chromium (Cr) (0.5 ppm), molybdenum (Mo) (50 ppb), and tungsten (W) (5 ppm) were not detected in any of the examples at their respective detection limits, as indicated in the parentheses following each element.
ND = not detected.

TABLE 10

1H NMR Data

| Sample | Vinyl/ 1000 C | Cis and Trans/ 1000 C | Trisubstituted/ 1000 C | Vinylidene/ 1000 C | Total Unsaturation/ 1000 C |
|---|---|---|---|---|---|
| IE 1 | 0.172 | 0.013 | 0.009 | 0.003 | 0.2 |
| IE 2 | 0.195 | 0.005 | 0.004 | 0.005 | 0.21 |
| Comp. B | 0.262 | 0.008 | 0.006 | 0.008 | 0.28 |

Film Properties

Cast Embossed Films

Monolayer cast embossed films using the inventive or comparative polyethylene compositions+12 wt. % LDPE 722+5 wt. % $TiO_2$ masterbatch were fabricated on a cast extrusion to reach 12 and 14 grams per square meter basis weight. Table 11 provides the film formulations. LDPE 722 has a density of 0.918 g/cc and melt index of 8 g/10 min, and is available from The Dow Chemical Company. The $TiO_2$ masterbatch comprises 70 wt. % $TiO_2$ and 30 wt. % polyethylene, and is available from Ampacet Corp. The LDPE and $TiO_2$ masterbatch were dry blended with the polyethylene composition prior to extrusion. Films were fabricated at a melt temperature of 255° C. with at a rate of 220 m/min, 400 kg/hr for 14 gsm films, and a rate of 220 m/min, 350 kg/hr for 12 gsm films. The bath quench temperature was 40° C.

TABLE 11

Film Formulations

| | |
|---|---|
| Film 1 | 83% IE 1; 12% LDPE 722; and 5% $TiO_2$ Masterbatch |
| Film 2 | 83% IE 2; 12% LDPE 722; and 5% $TiO_2$ Masterbatch |
| Film A | 83% Comp. A; 12% LDPE 722; and 5% $TiO_2$ Masterbatch |
| Film B | 83% Comp. B; 12% LDPE 722; and 5% $TiO_2$ Masterbatch |

TABLE 12

| Cast Embossed Film Data | | | | | | | | |
|---|---|---|---|---|---|---|---|---|
| Test | | Film A | Film 1 | Film 2 | Film B | Film 1 | Film 2 | Film B |
| Basis Weight (gsm) | | 14 | 14 | 14 | 14 | 12 | 12 | 12 |
| Spencer Dart Impact ($g_f$) | | 102 | 75 | 102 | 107 | 76 | 103 | 92 |
| Elmendorf | MD | 11 | 9 | 14 | 13 | 9 | 12 | 13 |
| Tear ($g_f$) | CD | 140 | 104 | 101 | 118 | 75 | 101 | 113 |
| Force to Draw to 1% (N) | MD | 112 | 122 | 102 | 117 | 115 | 84 | 82 |
| | CD | 118 | 114 | 94 | 118 | 125 | 95 | 80 |
| Force to Draw to 2% (N) | MD | 101 | 109 | 89 | 103 | 102 | 76 | 73 |
| | CD | 106 | 102 | 83 | 103 | 107 | 83 | 72 |
| Puncture (kJ/cm$^3$) | | 275 | 240 | 228 | 264 | 235 | 251 | 251 |
| Stress at Break (N) | MD | 7.6 | 6.6 | 7.8 | 7.7 | 5.7 | 6.4 | 6.7 |
| | CD | 5.1 | 4.8 | 6.3 | 6.4 | 4.4 | 5.4 | 5.3 |
| Strain at Break (%) | MD | 404 | 459 | 461 | 397 | 449 | 442 | 450 |
| | CD | 473 | 479 | 559 | 534 | 522 | 525 | 560 |

As shown in Table 12, at 12 gsm, inventive Film 1 and inventive Film 2 retain their Force to Draw to 2% in both MD and CD (as compared to their values at 14 gsm), while comparative Film B does not retain a comparable Force to Draw to 2% value at 12 gsm and 14 gsm. Also, inventive Film 1 and inventive Film 2 retain comparable dart impact values at 12 gsm as compared to their values at 14 gsm, while comparative Film B does not.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A cast film comprising a polyethylene composition comprising a reaction product of ethylene and optionally one or more alpha-olefin comonomers, wherein said polyethylene composition is characterized by the following properties:
   a. a melt index, 12, measured according to ASTM D 1238 (2.16 kg, 190° C.), of from 1 to 20 g/10 min;
   b. a density (measured according to ASTM D792) of from 0.940 to 0.970 g/cm$^3$;
   c. a melt flow ratio, $I_{10}/I_2$, wherein $I_{10}$ is measured according to ASTM D1238 (10 kg, 190° C.) of from 5.5 to 7.0;
   d. a molecular weight distribution ($M_w/M_n$) of from 2.2 to 3.5; and
   e. a vinyl unsaturation of greater than 0.12 vinyls per one thousand carbon atoms present in a backbone of the polyethylene composition;
   and wherein the cast film further comprises a low density polyethylene having a melt index, $I_2$ range of from 0.1 to 20 g/10 min.

2. The cast film of claim 1, wherein the cast film comprises from 5 to 30% of the low density polyethylene.

3. The cast film of claim 1, wherein the polyethylene composition is formed in the presence of a catalyst composition comprising a multi-metallic procatalyst via solution polymerization in at least one reactor.

4. The cast film of claim 3, wherein the solution polymerization occurs in a single reactor.

5. The cast film of claim 3, wherein the polyethylene composition has a metal catalyst residual of greater than or equal to 1 parts by combined weight of at least three metal residues per one million parts of polyethylene polymer, wherein the at least three metal residues are selected from the group consisting of titanium, zirconium, hafnium, vanadium, niobium, tantalum, chromium, molybdenum, tungsten, and combinations thereof, and wherein each of the at least three metal residues is present at greater than or equal to 0.2 ppm.

6. The cast film of claim 3, wherein the multi-metallic procatalyst has an Al:Ti ratio of from 6 to 15.

7. The cast film of claim 1, wherein the cast film is a monolayer film.

8. The cast film of claim 1, wherein the cast film is a multilayer film.

9. The cast film of claim 1, wherein the cast film is a cast embossed film.

10. A laminate comprising the cast film of claim 1.

11. An article made from the cast film according to claim 1.

* * * * *